(12) United States Patent
Kobayashi

(10) Patent No.: US 10,441,520 B2
(45) Date of Patent: *Oct. 15, 2019

(54) CLEANING AGENT COMPOSITION CONTAINING ACYL BASIC AMINO ACID DERIVATIVE

(71) Applicant: AJINOMOTO CO., INC., Tokyo (JP)

(72) Inventor: Shun Kobayashi, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 44 days.

This patent is subject to a terminal disclaimer.

(21) Appl. No.: 15/631,943

(22) Filed: Jun. 23, 2017

(65) Prior Publication Data

US 2017/0281497 A1    Oct. 5, 2017

Related U.S. Application Data

(63) Continuation of application No. PCT/JP2015/086209, filed on Dec. 25, 2015.

(30) Foreign Application Priority Data

Dec. 25, 2014    (JP) .................................. 2014-262416

(51) Int. Cl.

| | | |
|---|---|---|
| C11D 1/10 | (2006.01) | |
| A61K 8/44 | (2006.01) | |
| A61Q 5/02 | (2006.01) | |
| A61Q 19/10 | (2006.01) | |
| C09K 3/00 | (2006.01) | |
| A61K 8/36 | (2006.01) | |
| A61K 8/42 | (2006.01) | |
| A61K 8/60 | (2006.01) | |
| A61Q 5/12 | (2006.01) | |
| C11D 1/37 | (2006.01) | |
| C11D 1/83 | (2006.01) | |
| C11D 1/94 | (2006.01) | |
| C11D 3/00 | (2006.01) | |
| C11D 10/04 | (2006.01) | |

(52) U.S. Cl.

CPC ................. *A61K 8/44* (2013.01); *A61K 8/36* (2013.01); *A61K 8/42* (2013.01); *A61K 8/604* (2013.01); *A61Q 5/02* (2013.01); *A61Q 5/12* (2013.01); *A61Q 19/10* (2013.01); *C09K 3/00* (2013.01); *C11D 1/37* (2013.01); *C11D 1/83* (2013.01); *C11D 1/94* (2013.01); *C11D 3/0094* (2013.01); *C11D 10/04* (2013.01); *C11D 1/10* (2013.01)

(58) Field of Classification Search

CPC .... C11D 1/10; C11D 1/37; C11D 1/90; C11D 3/227

USPC ................. 510/119, 475, 490, 499

See application file for complete search history.

(56) References Cited

U.S. PATENT DOCUMENTS

| | | | |
|---|---|---|---|
| 2003/0069163 A1* | 4/2003 | Oshimura | A61K 8/44 510/490 |
| 2004/0248812 A1* | 12/2004 | Hanabusa | C09D 5/04 514/18.8 |
| 2012/0034181 A1* | 2/2012 | Hoffmann | A61K 8/416 424/70.9 |
| 2014/0348767 A1 | 11/2014 | Hanabusa et al. | |
| 2014/0350128 A1 | 11/2014 | Hanabusa et al. | |
| 2017/0137372 A1* | 5/2017 | Kobayashi | C07C 233/47 |
| 2017/0281494 A1* | 10/2017 | Haraya | A61K 8/42 |
| 2017/0281495 A1* | 10/2017 | Haraya | A61K 8/44 |
| 2017/0281496 A1* | 10/2017 | Haraya | A61K 8/44 |
| 2017/0281497 A1* | 10/2017 | Kobayashi | A61K 8/44 |
| 2017/0281510 A1* | 10/2017 | Kobayashi | A61K 8/34 |

FOREIGN PATENT DOCUMENTS

| | | | | |
|---|---|---|---|---|
| EP | 1 473 027 A1 | 11/2004 | | |
| EP | 1473027 A1 * | 11/2004 | ............... | C09D 5/04 |
| JP | 4-372700 A | 12/1992 | | |
| JP | 7-216385 A | 8/1995 | | |
| JP | 2002-322497 A | 11/2002 | | |
| JP | 2004-323505 A | 11/2004 | | |

(Continued)

OTHER PUBLICATIONS

The Supplementary European Search Report dated Aug. 13, 2018 in Patent Application 15873260.2, 7 pages.

(Continued)

*Primary Examiner* — Gregory E Webb

(74) *Attorney, Agent, or Firm* — Oblon, McClelland, Maier & Neustadt, L.L.P.

(57) ABSTRACT

The present invention provides a composition containing component (A): a compound represented by the formula (1)

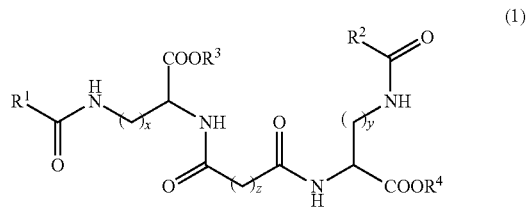

wherein each symbol is as described in the DESCRIPTION, or a salt thereof, and component (B): at least one kind of surfactant selected from the group consisting of an anionic surfactant having a carboxyl group, an amphoteric surfactant and a nonionic surfactant, which is superior in foamability and foam volume and affording improved rinsing performance and smooth feeling after drying.

15 Claims, No Drawings

(56) References Cited

FOREIGN PATENT DOCUMENTS

WO WO 2013/118895 A1 8/2013
WO WO 2013/118896 A1 8/2013

OTHER PUBLICATIONS

Yaqin Liang, et al., "Surface Adsorption and Aggregation Properties of Novel L-Lysine-Based Gemini Surfactants", Journal of Surfactants and Detergents, vol. 17, No. 4, XP055426540, Jul. 1, 2014, pp. 693-701.
Masahiro Suzuki, et al., "L-Lysine based gemini organogelators: their organogelation properties and thermally stable organogels," Org. Biomol Chem, vol. 1, 2003, 4124-4131.
Masahiro Suzuki, et al., "Novel Dumbbell-form low-molecular-weight gelators based on L-Lysine: their hydrogelation and organogelation properties," New J. Chem, vol. 29, 2005, 1439-1444.

* cited by examiner

CLEANING AGENT COMPOSITION CONTAINING ACYL BASIC AMINO ACID DERIVATIVE

CROSS REFERENCES TO RELATED APPLICATIONS

This application is a continuation of International Patent Application No. PCT/JP2015/086209, filed on Dec. 25, 2015, and claims priority to Japanese Patent Application No. 10 2014-262416, filed on Dec. 25, 2014, all of which are incorporated herein by reference in their entireties.

BACKGROUND OF THE INVENTION

Field of the Invention

The present invention relates to a composition containing (A): an acyl basic amino acid derivative and (B): at least one kind of surfactant selected from the group consisting of an anionic surfactant having a carboxyl group, an amphoteric surfactant and a nonionic surfactant, which is used as, for example, a cleaning agent.

Discussion of the Background

As a surfactant to be blended in cleaning agents such as shampoo and the like, 1) anionic surfactants such as acyl neutral amino acid salt, acyl acidic amino acid salt and the like, 2) amphoteric surfactants such as alkyl betaines and fatty acid amidopropyl betaines, or 3) nonionic surfactants such as alkyl polyglucoside and the like has been added. However, these surfactants are actually not satisfactory due to foamability, foam volume, poor rinsing off performance, stickiness, insufficient smooth feeling after drying and the like as compared to anionic surfactants such as alkylsulfuric acid ester salt, polyoxyethylenealkylethersulfate, alkylbenzenesulfonate and the like used conventionally.

Generally, a water insoluble powder is sometimes added to a cleaning agent to improve foamability, foam volume, easy rinsing off during cleansing and texture after use (patent document 1). Furthermore, a technique for dispersing a water insoluble powder in a liquid cleansing agent is also known (patent document 2). However, a transparent cleaning agent cannot be obtained due to the use of a water insoluble powder, and the use thereof is restricted.

It has been reported that a compound represented by the following formula:

wherein $R^a$ and $R^b$ are each a hydrogen atom or an alkyl group, and n is an integer of 0 to 12, or a salt thereof (hereinafter to be also referred to as "lauroyl amino acid derivative") is useful for gelation or solidifying water and a liquid organic medium (patent document 3, non-patent document 1 and non-patent document 2 etc.).

However, a composition containing a lauroyl amino acid derivative and a surfactant, and a cleaning agent containing the composition have not been reported heretofore.

DOCUMENT LIST

Patent Documents patent document 1: JP-A-4-372700
patent document 2: JP-A-7-216385
patent document 3: JP-A-2004-323505

Non-Patent Documents non-patent document 1: Org. Biomol. Chem., 2003, 1, 4124-4131
non-patent document 2: New J. Chem., 2005, 29, 1439-1444

SUMMARY OF THE INVENTION

Problems to be Solved by the Invention

An object of the present invention is to provide a composition superior in the foamability and the foam volume, which improves rinsing performance and smooth feeling after drying.

Means of Solving the Problems

The present inventor has conducted intensive studies in an attempt to achieve the above-mentioned object and unexpectedly found that foamability and foam volume can be made fine and rinsing performance and smooth feeling after drying can be improved by only adding component (A): a compound represented by the following formula (1) (hereinafter sometimes to be also referred to as "compound (1)") or a salt thereof to component (B): at least one kind of surfactant selected from the group consisting of an anionic surfactant having a carboxyl group, an amphoteric surfactant and a nonionic surfactant, which resulted in the completion of the present invention.

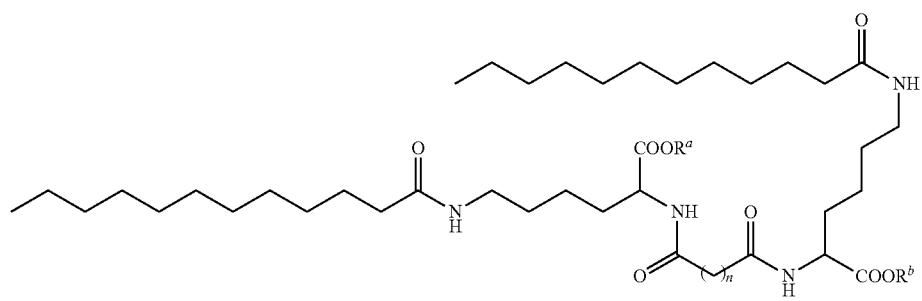

Therefore, the present invention provides the following.
[1] A composition comprising component (A): a compound represented by the formula (1)

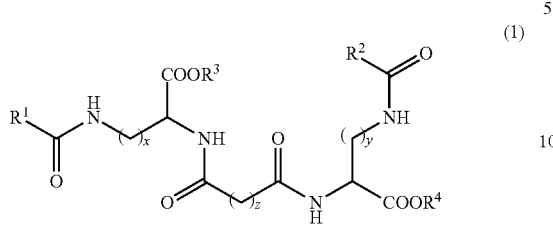

wherein
$R^1$ and $R^2$ are each independently an alkyl group having 5-21 carbon atoms or an alkenyl group having 5-21 carbon atoms,
$R^3$ and $R^4$ are each independently a hydrogen atom, an alkyl group having 1-22 carbon atoms or an alkenyl group having 2-22 carbon atoms,
z is an integer of not less than 0,
x and y are each independently an integer of 2-4, or a salt thereof, and
component (B): at least one kind of surfactant selected from the group consisting of an anionic surfactant having a carboxyl group, an amphoteric surfactant and a nonionic surfactant.
[2] The composition of [1], wherein component (A) is a compound of the aforementioned formula (1) wherein z is an integer of 0-10, or a salt thereof.
[3] The composition of [1] or [2], wherein component (A) is a compound of the aforementioned formula (1) wherein z is 7 or 8, or a salt thereof.
[4] The composition of any of [1]-[3], wherein component (A) is a compound of the aforementioned formula (1) wherein x and y are each 4, or a salt thereof.
[5] The composition of any of [1]-[4], wherein component (A) is a compound of the aforementioned formula (1) wherein $R^1$ and $R^2$ are each independently a straight-chain alkyl group having 5-15 carbon atoms, or a salt thereof.
[6] The composition of any of [1]-[5], wherein component (A) is a compound of the aforementioned formula (1) wherein $R^3$ and $R^4$ are each a hydrogen atom, or a salt thereof.
[7] The composition of any of [1]-[5], wherein component (A) is a compound of the aforementioned formula (1) wherein $R^1$ and $R^2$ are each independently a straight-chain alkyl group having 5-15 carbon atoms, $R^3$ and $R^4$ are each a hydrogen atom, z is an integer of 0-10, and x and y are each 4, or a salt thereof.
[8] The composition of any of [1]-[5], wherein component (A) is a compound of the aforementioned formula (1) wherein $R^1$ and $R^2$ are each a straight-chain alkyl group having 5-15 carbon atoms, $R^3$ and $R^4$ are each a hydrogen atom, z is 7 or 8, and x and y are each 4, or a salt thereof.
[9] The composition of any of [1]-[8], wherein component (A) is a compound selected from bis($N^\varepsilon$-lauroyl-L-lysine) sebacoyl amide or a salt thereof, and bis($N^\varepsilon$-octanoyl-L-lysine)sebacoyl amide, or a salt thereof.
[10] The composition of any of [1]-[9], wherein the component (A) is contained in a proportion of 0.01-10 wt % relative to the total amount of the composition.
[11] The composition of any of [1]-[10], wherein the anionic surfactant having a carboxyl group is at least one kind selected from the group consisting of a fatty acid salt, an alkyl ether carboxylate, a hydroxyalkyl ether carboxylate, an acyl acidic amino acid salt and an acyl neutral amino acid salt.
[12] The composition of any of [1]-[10], wherein the amphoteric surfactant is at least one kind selected from the group consisting of an amino acetic acid betaine surfactant, an imidazolinium betaine surfactant, an alkyl betaine surfactant, a fatty acid amidopropyl betaine surfactant and a sultaine surfactant.
[13] The composition of any of [1]-[10], wherein the nonionic surfactant is alkyl polyglucoside.
[14] The composition of any of [1]-[13], wherein the component (B) is contained in a proportion of 0.01-50 wt % relative to the total amount of the composition.
[15] A cleaning agent comprising the composition of any of [1]-[14].

Effect of the Invention

According to the present invention, a composition superior in the foamability and the foam volume, which improves rinsing performance and smooth feeling after drying can be provided.

DETAILED DESCRIPTION OF THE PREFERRED EMBODIMENTS

The composition of the present invention is characterized in that it is a composition containing component (A): a compound represented by the formula (1)

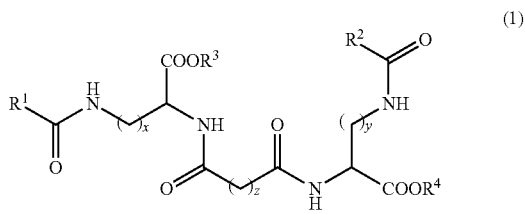

wherein
$R^1$ and $R^2$ are each independently an alkyl group having 5-21 carbon atoms or an alkenyl group having 5-21 carbon atoms,
$R^3$ and $R^4$ are each independently a hydrogen atom, an alkyl group having 1-22 carbon atoms or an alkenyl group having 2-22 carbon atoms,
z is an integer of not less than 0,
x and y are each independently an integer of 2-4, or a salt thereof, and
component (B): at least one kind of surfactant selected from the group consisting of an anionic surfactant having a carboxyl group, an amphoteric surfactant and a nonionic surfactant.

The embodiment of the present invention is described in detail in the following.

1. Component (A): A Compound Represented by the Formula (1) (Compound (1)) or a Salt Thereof $R^1$ and $R^2$ are each independently an alkyl group having 5-21 carbon atoms or an alkenyl group having 5-21 carbon atoms.

The alkyl group having 5-21 carbon atoms means a straight-chain or branched-chain alkyl group having 5-21 carbon atoms. Specific examples thereof include pentyl group, isopentyl group, neopentyl group, a hexyl group, isohexyl group, neohexyl group, heptyl group, isoheptyl group, neoheptyl group, octyl group, isooctyl group, nonyl group, isononyl group, decyl group, isodecyl group, undecyl group, dodecyl group, tridecyl group, tetradecyl group, pentadecyl group, hexadecyl group, heptadecyl group, octadecyl group, nonadecyl group, icosyl group and the like.

The alkenyl group having 5-21 carbon atoms means a straight-chain or branched-chain alkenyl group having 5-21 carbon atoms. Specific examples thereof include pentenyl group, hexenyl group, heptenyl group, octenyl group, nonenyl group, decenyl group, undecenyl group, dodecenyl group, tridecenyl group, tetradecenyl group, pentadecenyl group, hexadecenyl group, heptadecenyl group, octadecenyl group, nonadecenyl group, icosenyl group and the like.

An alkyl group having 5-15 carbon atoms means a straight-chain or branched-chain alkyl group having 5-15 carbon atoms. Specific examples thereof include pentyl group, a hexyl group, heptyl group, octyl group, nonyl group, decyl group, undecyl group, dodecyl group, tridecyl group, tetradecyl group, pentadecyl group and the like.

An alkyl group having 7-11 carbon atoms means a straight-chain or branched-chain alkyl group having 7-11 carbon atoms. Specific examples thereof include heptyl group, octyl group, nonyl group, decyl group, undecyl group and the like.

$R^1$ and $R^2$ are preferably each independently an alkyl group having 5-15 carbon atoms, more preferably each independently an alkyl group having 7-11 carbon atoms.

Preferably, $R^1$ and $R^2$ are each a straight-chain alkyl group. Furthermore, $R^1$ and $R^2$ are preferably the same.

$R^3$ and $R^4$ are each independently a hydrogen atom, an alkyl group having 1-22 carbon atoms or an alkenyl group having 2-22 carbon atoms.

An alkyl group having 1-22 carbon atoms means a straight-chain or branched-chain alkyl group having 1-22 carbon atoms. Specific examples thereof include methyl group, an ethyl group, a propyl group, an isopropyl group, a butyl group, an isobutyl group, a sec-butyl group, a tert-butyl group, a pentyl group, isopentyl group, neopentyl group, a hexyl group, isohexyl group, neohexyl group, heptyl group, isoheptyl group, neoheptyl group, octyl group, isooctyl group, nonyl group, isononyl group, decyl group, isodecyl group, undecyl group, dodecyl group, tridecyl group, tetradecyl group, pentadecyl group, hexadecyl group, heptadecyl group, octadecyl group, nonadecyl group, icosyl group and the like.

An alkenyl group having 2-22 carbon atoms means a straight-chain or branched-chain alkenyl group having 2-22 carbon atoms. Specific examples thereof include ethenyl group, 1-propenyl group, 2-propenyl group, 1-butenyl group, 2-butenyl group, 3-butenyl group, pentenyl group, hexenyl group, heptenyl group, octenyl group, nonenyl group, decenyl group, undecenyl group, dodecenyl group, tridecenyl group, tetradecenyl group, pentadecenyl group, hexadecenyl group, heptadecenyl group, octadecenyl group, nonadecenyl group, icosenyl group and the like.

Preferably, both $R^3$ and $R^4$ are hydrogen atoms.

z is an integer of not less than 0.

z is preferably an integer of 0-10, more preferably 7 or 8.

x and y are each independently an integer of 2-4.

x and y are each preferably 4.

As a compound represented by the formula (1), the following compounds can be preferably recited.

(Compound A)

A compound wherein $R^1$ and $R^2$ are each independently a straight-chain alkyl group having 5-15 carbon atoms, $R^3$ and $R^4$ are each a hydrogen atom, z is an integer of 0-10, and x and y are each 4.

(Compound B)

A compound wherein $R^1$ and $R^2$ are each a straight-chain alkyl group having 5-15 carbon atoms, $R^3$ and $R^4$ are each a hydrogen atom, z is 7 or 8, and x and y are each 4.

(Compound C)

A compound wherein $R^1$ and $R^2$ are each a straight-chain alkyl group having 7-11 carbon atoms, $R^3$ and $R^4$ are each a hydrogen atom, z is 7 or 8, and x and y are each 4.

Specific examples of the compound represented by the formula (1) include bis($N^\varepsilon$-lauroyl-L-lysine)sebacoyl amide, bis($N^\varepsilon$-octanoyl-L-lysine)sebacoyl amide, and a salt thereof.

The salt of the compound represented by the formula (1) is not particularly limited. Examples thereof include alkali metal salts such as sodium salt, potassium salt and the like, alkaline earth metal salts such as calcium salt, magnesium salt and the like, inorganic salts such as aluminum salt, salt with zinc and the like, and organic salts such as organic amine salts such as ammonium salt, monoethanolamine salt, diethanolamine salt, triethanolamine salt and the like, basic amino acid salts such as arginine salt, lysine salt and the like, and the like. One kind of these may be used, or two or more kinds selected from the above-mentioned group may be used in a mixture. From the aspects of easy availability, handling property and the like, alkali metal salt, organic amine salt, or basic amino acid salt is preferable, and sodium salt and potassium salt are particularly preferable.

Compound (1) can be produced by a method known per se or a method analogous thereto (JP-A-2004-323505, Org. Biomol. Chem., 2003, 1, 4124-4131, New J. Chem., 2005, 29, 1439-1444 etc.). For example, as shown in the following formula, of compounds (1), symmetrical compound (1') can be produced by reacting $N^\omega$-acyl amino acid (2) and dicarboxylic acid dichloride (3) in an appropriate solvent.

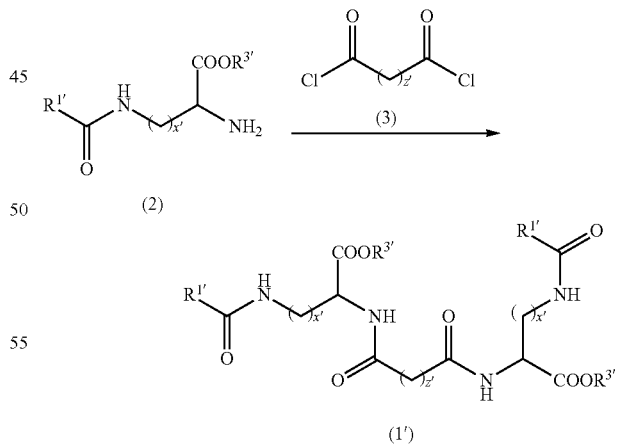

wherein $R^{1'}$ is an alkyl group having 5-21 carbon atoms or an alkenyl group having 5-21 carbon atoms, $R^{3'}$ is a hydrogen atom, an alkyl group having 1-22 carbon atoms or an alkenyl group having 2-22 carbon atoms, z' is an integer of not less than 0, and x' is an integer of 2-4.

Examples of the $N^\omega$-acyl amino acid (2) include $N^\varepsilon$-acyl lysine (e.g., $N^\varepsilon$-hexanoyl-L-lysine, $N^\varepsilon$-octanoyl-L-lysine etc.), $N^δ$-acyl ornithine (e.g., $N^δ$-hexanoyl-L-ornithine etc.), $N^γ$-acyl-α,γ-diaminobutyric acid and the like.

Examples of the dicarboxylic acid dichloride (3) include oxalyl chloride, malonyl chloride, succinyl chloride, glutaryl chloride, adipoyl chloride, pimeloyl chloride, suberoyl chloride, azelaoyl chloride, sebacoyl chloride, dodecanedioyl chloride and the like. The amount of dicarboxylic acid dichloride (3) to be used is generally 0.4-0.6 equivalent relative to $N^ω$-acyl amino acid (2).

While the solvent is not particularly limited as long as it is inert to the reaction, examples thereof include ethers such as diethyl ether, tetrahydrofuran and the like.

In addition, of compounds (1), asymmetric compound (1″) can be produced as follows. First, $N^ω$-acyl amino acid (2) and dicarboxylic acid monochloride monoester (4) are reacted in an appropriate solvent to give compound (5) (step 1). Then, the primary ester moiety of the obtained compound (5) is hydrolyzed in the presence of a base such as sodium hydroxide, potassium hydroxide and the like, the carboxylic acid moiety is chlorinated with a chlorinating agent such as thionyl chloride and the like, and the compound is reacted with $N^ω$-acyl amino acid (2') which is different from $N^ω$-acyl amino acid (2) used in the aforementioned step 1 (step 2), whereby derivative (1″) can be produced.

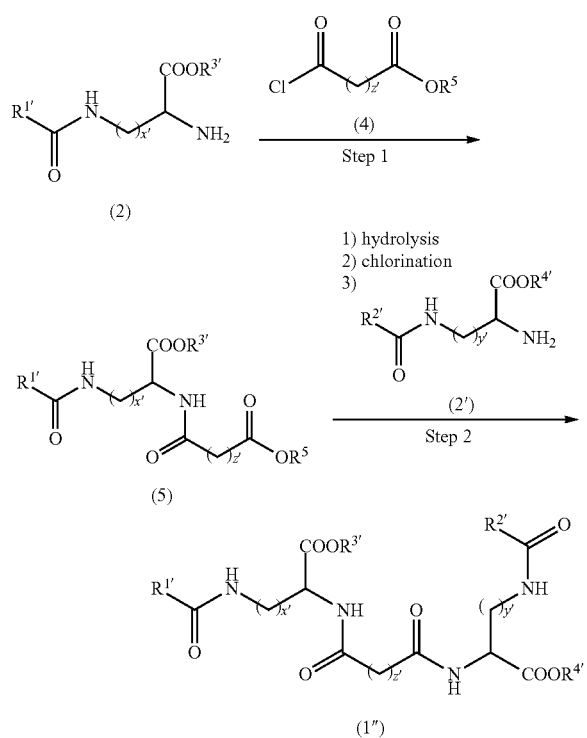

wherein $R^{1'}$, $R^{3'}$, z' and x' are as defined above, $R^{2'}$ is an alkyl group having 5-21 carbon atoms or an alkenyl group having 5-21 carbon atoms, $R^{4'}$ is a hydrogen atom, an alkyl group having 1-22 carbon atoms or an alkenyl group having 2-22 carbon atoms, $R^5$ is an alkyl group such as a methyl group, an ethyl group and the like, and y' is an integer of 2-4.

As $N^ω$-acyl amino acids (2) and (2'), $N^ω$-acyl amino acids similar to those mentioned above can be used.

As dicarboxylic acid monochloride monoester (4), a commercially available product can be used as is, or one produced by a method known per se or a method analogous thereto can also be used.

Compound (1) obtained by the aforementioned method can be converted to a salt of compound (1) by a reaction with alkali metal hydroxide such as sodium hydroxide, potassium hydroxide and the like, alkali earth metal hydroxide such as calcium hydroxide and the like, organic amine base, or the like.

The content of component (A): compound (1) or a salt thereof in the composition of the present invention is generally 0.01-10 wt %, preferably 0.01-5 wt %, relative to total amount of the composition.

2. Component (B): at Least One Kind of Surfactant Selected From the Group Consisting of an Anionic Surfactant Having a Carboxyl Group, an Amphoteric Surfactant and a Nonionic Surfactant Specific examples of the "anionic surfactant having a carboxyl group" in the present specification include fatty acid salt, alkyl ether carboxylate, hydroxyalkyl ether carboxylate, acyl acidic amino acid salt, acyl neutral amino acid salt and the like.

Examples of the fatty acid of the fatty acid salt include a saturated or unsaturated fatty acid having 8-22 carbon atoms, specifically, caprylic acid, capric acid, lauric acid, myristic acid, stearic acid, isostearic acid, palmitic acid, oleic acid, linoleic acid, linolenic acid, behenic acid, coconut oil fatty acid, palm fatty acid, palm kernel fatty acid, hardened beef tallow fatty acid and the like. Of these, one kind may be used, or two or more kinds selected from the above-mentioned group may be mixed and used. Particularly, lauric acid, myristic acid, palmitic acid and stearic acid are preferable. Specific examples of the fatty acid salt include sodium salt and potassium salt (e.g., potash soap material etc.) of the above-mentioned fatty acid, and the like.

Examples of the alkyl ether carboxylic acid of the alkyl ether carboxylate include a compound represented by the formula (6):

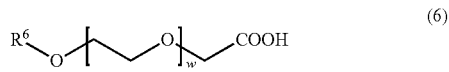

wherein $R^6$ is a saturated or unsaturated hydrocarbon group having 8-22 carbon atoms, w is an integer of 2-20). Specific examples thereof include polyoxyethylene (EO4) lauryl ether acetic acid, polyoxyethylene (EO4) lauryl ether sodium acetate, polyoxyethylene (EO5) lauryl ether sodium acetate, polyoxyethylene (EO4) tridecyl ether acetic acid, polyoxyethylene (EO4) tridecyl ether sodium acetate, polyoxyethylene (EO7) tridecyl ether sodium acetate, polyoxyethylene (EO11) lauryl ether sodium acetate and the like. Of these, polyoxyethylene (EO4) lauryl ether sodium acetate, polyoxyethylene (EO5) lauryl ether sodium acetate, and polyoxyethylene (EO11) lauryl ether sodium acetate are preferable. Of these, one kind may be used, or two or more kinds selected from the above-mentioned group may, be mixed and used.

Examples of the hydroxyalkyl ether carboxylic acid of the hydroxyalkyl ether carboxylate include a compound represented by the formula (7):

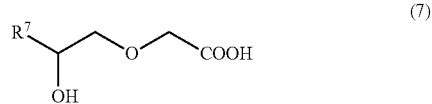

wherein $R^7$ is a saturated or unsaturated hydrocarbon group having 8-22 carbon atoms. Specific examples thereof include sodium lauryl glycol carboxylate, potassium tridecyl glycol carboxylate and the like. Among them, sodium lauryl glycol carboxylate is preferable. Of these, one kind thereof may be used, or two or more kinds selected from the above-mentioned group may be mixed and used.

As the acyl group of the acyl acidic amino acid salt and acyl neutral amino acid salt, a straight-chain or branched-chain chain acyl group induced from a saturated or unsaturated fatty acid having 8-22 carbon atoms can be used. As fatty acid, for example, the fatty acid and the like recited above can be mentioned. As the acidic amino acid of the acyl acidic amino acid salt, glutamic acid, aspartic acid and the like can be mentioned; and as the neutral amino acid of the acyl neutral amino acid salt, glycine, sarcosine, β-alanine and the like can be mentioned. As the acyl acidic amino acid, cocoylglutamic acid (coconut oil fatty acid glutamic acid) is preferable, and as the acyl neutral amino acid, cocoylglycine (coconut oil fatty acid glycine) is preferable.

The fatty acid salt, alkyl ether carboxylate, hydroxyalkyl ether carboxylate, acyl acidic amino acid salt and acyl neutral amino acid salt are not particularly limited. Examples thereof include alkali metal salts such as sodium salt, potassium salt and the like, alkaline earth metal salts such as calcium salt, magnesium salt and the like, inorganic salts such as aluminum salt, salt with zinc and the like, and organic salts such as organic amine salts such as ammonium salt, monoethanolamine salt, diethanolamine salt, triethanolamine salt and the like, basic amino acid salts such as arginine salt, lysine salt and the like, and the like. One kind of these may be used, or two or more kinds selected from the above-mentioned group may be used in a mixture. From the aspects of easy availability, handling property and the like, alkali metal salt, organic amine salt, or basic amino acid salt is preferable, and sodium salt is particularly preferable.

Specific examples of the "amphoteric surfactant" in the present specification include amino acetic acid betaine surfactant (e.g., lauryl dimethyl amino acetic acid betaine, coconut oil dimethyl amino acetic acid betaine, lauric acid amidopropyl dimethyl amino acetic acid betaine, coconut oil fatty acid amidopropyl dimethyl amino acetic acid betaine, hydroxyalkyl(C12-14)hydroxyethyl sarcosine, lauric acid amidopropyl hydroxy sulfobetaine, lauryl hydroxy sulfobetaine), imidazolinium betaine surfactant (e.g., cocoamphoacetic acid, lauroamphoacetic acid, cocoamphodiacetic acid, lauroamphodiacetic acid, lauramidopropionic acid etc.), alkyl betaine surfactant, fatty acid amidopropyl betaine surfactant (e.g., cocamidopropyl betaine etc.), sultaine surfactant and the like.

Specific examples of the "nonionic surfactant" in the present specification include alkyl polyglucoside (e.g., decylglucoside, lauryl glucoside, cocoglucoside) and the like.

In the composition of the present invention, the content of component (B): at least one kind of surfactant selected from the group consisting of an anionic surfactant having a carboxyl group, an amphoteric surfactant and a nonionic surfactant is generally 0.01-50 wt % relative to the total amount of the composition.

In the composition of the present invention, the weight of component (A)/weight of component (B) is generally 0.0001-1.

While the pH of the composition of the present invention is not particularly limited, pH 5-11 is preferable.

The present invention also relates to a cleaning agent containing the aforementioned composition of the present invention.

As the cleaning agent of the present invention, facial cleanser, soap, body shampoo, shampoo, hand soap and the like can be specifically mentioned.

The cleaning agent of the present invention may contain components that can be generally added to a cleaning agent, as long as the effect of the present invention is not inhibited. Specific examples include oil, chelating agent, amino acids, polyamino acid and salt thereof, water-soluble polymer, sugar alcohol and alkylene oxide adduct thereof, lower alcohol, animal and plant extract, nucleic acid, vitamin, enzyme, anti-inflammatory agent, antimicrobial agent, preservative, antioxidant, ultraviolet absorber, adiaphoretic, pigment, dye, oxidation dye, pH adjuster, pearly sheen agent, wetting agent and the like.

The composition of the present invention, and a cleaning agent containing the composition can be produced according to a conventional method.

Other features of the invention will become apparent in the course of the following descriptions of exemplary embodiments which are given for illustration of the invention and are not intended to be limiting thereof.

EXAMPLES

The present invention is concretely explained in the following by referring to Examples. The present invention is not limited by the following Examples. Unless particularly indicated, "%" means "wt %".

Production Example 1

Synthesis of bis($N^\varepsilon$-lauroy-L-lysine)sebacoylamide disodium salt $N^\varepsilon$-lauroyl-L-lysine (8.2 g, 25 mmol) was dissolved in water (70 g) and 25% aqueous sodium hydroxide solution (10 g), and diethyl ether (80 g) was added. Sebacoyl chloride (3.3 g, 14 mmol) was slowly added to the ether layer. The two-layer solution was stirred for about 1 hr while maintaining at 0° C., and then at room temperature for 23 hr. Then, 75% sulfuric acid was added dropwise to adjust to pH 2, the obtained white precipitate was collected by filtration, washed well with water and dried. The obtained compound was dissolved in an aqueous sodium hydroxide solution to give a 10% aqueous bis($N^\varepsilon$-lauroyl-L-lysine)sebacoyl amide disodium salt solution.

Production Example 2

Synthesis of bis($N^\varepsilon$-octanoyl-L-lysine)sebacoylamide disodium salt $N^\varepsilon$-octanoyl-L-lysine (6.8 g, 25 mmol) was dissolved in water (70 g) and 25% aqueous sodium hydroxide solution (10 g), and diethyl ether (80 g) was added. Sebacoyl chloride (3.3 g, 14 mmol) was slowly added to the ether layer. The two-layer solution was stirred for about 1 hr while maintaining at 0° C., and then at room temperature for 23 hr. Then, 75% sulfuric acid was added dropwise to adjust to pH 2, the obtained white precipitate was collected by filtration, washed well with water and dried. The obtained compound was dissolved in an aqueous sodium hydroxide solution to give a 10% aqueous bis($N^\varepsilon$-octanoyl-L-lysine)sebacoyl amide disodium salt solution.

¹H-NMR of bis(Nᵉ-octanoyl-L-lysine)sebacoyl amide (free form) ¹H-NMR (400 MHz, DMSO-$d_6$, TMS, 25° C.): δ0.85 (t, J=6.8 Hz, 6H), 1.20-1.29 (m, 28H), 1.32-1.38 (m, 4H), 1.45-1.50 (m, 8H), 1.54-1.59 (m, 4H), 2.02 (t, J=7.4 Hz, 4H), 2.09 (t, J=7.4 Hz, 4H), 2.99 (q, J=6.5 Hz, 4H), 4.08-4.47 (m, 2H), 7.73 (t, J=5.6 Hz, 2H), 7.97 (d, J=8.0 Hz, 2H).

Experimental Example

Compositions having the blend compositions (the amounts in Examples and Comparative Examples are in wt %) shown in the following Table 1 were prepared by a conventional method (by adjusting to the pH in the Table with a pH adjuster (e.g., citric acid, lactic acid, glutamic acid) and adding a preservative (e.g., methylparaben, phenoxyethanol)), evaluated by professional 10 panelists for quick foaming, foam volume, quick rinsing performance and smooth feeling after drying, and marked according to the following criteria.

1) quick foaming
3 points: very good quick foaming
2 points: good quick foaming
1 point: normal quick foaming
0 point: bad quick foaming 2) foam volume
3 points: very good foam volume
2 points: good foam volume
1 point: normal foam volume
0 point: bad foam volume 3) quick rinsing performance
3 points: very good quick rinsing performance
2 points: good quick rinsing performance
1 point: normal quick rinsing performance
0 point: poor quick rinsing performance 4) smooth feeling after drying
3 points: very good smooth feeling after drying
2 points: good smooth feeling after drying
1 point: normal smooth feeling after drying
0 point: no smooth feeling after drying Each panelist made evaluation according to the above-mentioned criteria, and the points were averaged and the evaluation was classified according to the following indices.

⊙: average of points, not less than 2.2
○: average of points, not less than 1.5 and less than 2.2
×: average of points, not less than 0.8 and less than 1.5
×: average of points, less than 0.8

The results are shown in Table 1.

TABLE 1

| | | Ex. 1 | Ex. 2 | Ex. 3 | Ex. 4 | Ex. 5 | Ex. 6 | Ex. 7 |
|---|---|---|---|---|---|---|---|---|
| component (A) | compound of Production Example 1 (10% aqueous solution) | 0.5 | 3 | — | 0.5 | 3 | — | 0.5 |
| | compound of Production Example 2 (10% aqueous solution) | — | — | 0.5 | — | — | 0.5 | — |
| component (B) | sodium cocoyl glutamate | 10 | 10 | 10 | — | — | — | — |
| | sodium cocoyl glycinate | — | — | — | 10 | 10 | 10 | — |
| | cocamidopropyl betaine | — | — | — | — | — | — | 10 |
| | decylglucoside | — | — | — | — | — | — | — |
| | potash soap material | — | — | — | — | — | — | — |
| | pH adjuster | adjusted to pH 5.0 | adjusted to pH 5.0 | adjusted to pH 5.0 | adjusted to pH 7.0 | adjusted to pH 7.0 | adjusted to pH 7.0 | adjusted to pH 5.0 |
| | preservative | q.s. | q.s. | q.s. | q.s. | q.s. | q.s. | q.s. |
| | water | balance | balance | balance | balance | balance | balance | balance |
| evaluation results | quick foaming | ⊙ | ⊙ | ⊙ | ⊙ | ⊙ | ⊙ | ⊙ |
| | foam volume | ○ | ○ | ○ | ⊙ | ⊙ | ⊙ | ⊙ |
| | quick rinsing performance | ○ | ⊙ | ○ | ○ | ⊙ | ○ | ○ |
| | smooth feeling after drying | ○ | ⊙ | ○ | ⊙ | ⊙ | ⊙ | ○ |

| | | Ex. 8 | Ex. 9 | Comp. Ex. 1 | Comp. Ex. 2 | Comp. Ex. 3 | Comp. Ex. 4 | Comp. Ex. 5 |
|---|---|---|---|---|---|---|---|---|
| component (A) | compound of Production Example 1 (10% aqueous solution) | 0.5 | 0.5 | — | — | — | — | — |
| | compound of Production Example 2 (10% aqueous solution) | — | — | — | — | — | — | — |
| component (B) | sodium cocoyl glutamate | — | — | 10 | — | — | — | — |
| | sodium cocoyl glycinate | — | — | — | 10 | — | — | — |
| | cocamidopropyl betaine | — | — | — | — | 10 | — | — |
| | decylglucoside | 10 | — | — | — | — | 10 | — |
| | potash soap material | — | 10 | — | — | — | — | 10 |
| | pH adjuster | adjusted to pH 6.0 | adjusted to pH 9.0 | adjusted to pH 5.0 | adjusted to pH 7.0 | adjusted to pH 5.0 | adjusted to pH 6.0 | adjusted to pH 9.0 |
| | preservative | q.s. | q.s. | q.s. | q.s. | q.s. | q.s. | q.s. |
| | water | balance | balance | balance | balance | balance | balance | balance |

TABLE 1-continued

| evaluation results | quick foaming | ⊙ | ⊙ | X | Δ | Δ | Δ | X |
|---|---|---|---|---|---|---|---|---|
| | foam volume | ⊙ | ○ | Δ | Δ | X | Δ | X |
| | quick rinsing performance | ○ | ⊙ | X | Δ | X | Δ | ○ |
| | smooth feeling after drying | ○ | ○ | Δ | Δ | Δ | Δ | X |

The compositions of the present invention (Examples 1-9) were very fine or good in all evaluation items of quick foaming, foam volume, quick rinsing performance and smooth feeling after drying.

Preferable blending examples of the composition of the present invention are explained below.

Blending Example 1 Cleansing Foam

A cleansing foam blended as shown in the following Table 2 was prepared according to a conventional method.

TABLE 2

| | wt % |
|---|---|
| sodium cocoyl glycinate, water | 33.00 |
| compound of Production Example 1 (10%) | 1.00 |
| xanthan gum | 0.10 |
| water | balance |
| glycerol | 30.00 |
| cocoglucoside, water | 2.00 |
| sodium citrate | 0.25 |
| preservative | q.s. |
| lauramidopropyl betaine, water | 13.00 |
| citric acid | 1.40 |
| total | 100.00 |

Blending Example 2 Gel Facial Cleanser

A gel facial cleanser blended as shown in the following Table 3 was prepared according to a conventional method.

TABLE 3

| | wt % |
|---|---|
| sodium cocoyl glutamate, disodium cocoyl glutamate, water | 25.00 |
| cocobetaine, water | 2.00 |
| sodium cocoamphoacetate, water | 1.60 |
| glyceryl caprylate | 2.50 |
| propanediol | 7.00 |
| sodium chloride | 0.30 |
| citric acid | 0.60 |
| compound of Production Example 1 (10%) | 1.00 |
| jojoba oil | 4.00 |
| almond oil | 4.00 |
| guar gum | 1.50 |
| water | balance |
| total | 100.00 |

Blending Example 3 Cleansing Foam

A cleansing foam blended as shown in the following Table was prepared according to a conventional method.

TABLE 4

| | wt % |
|---|---|
| sodium lauryl glycol carboxylate, water | 8.33 |
| phytosteryl/octyldodecyl lauroyl glutamate | 1.00 |
| glycerol | 6.00 |
| sorbitol | 14.00 |

TABLE 4-continued

| | wt % |
|---|---|
| PEG-32 | 10.00 |
| compound of Production Example 1 (10%) | 1.00 |
| beeswax | 1.00 |
| stearic acid | 12.00 |
| lauric acid | 3.00 |
| myristic acid | 7.00 |
| poloxamer 184 | 2.00 |
| isostearic acid PEG-90 glyceryl | 3.00 |
| glyceryl stearate (SE) | 1.50 |
| sodium methyl cocoyl taurate, water | 25.00 |
| lauryl betaine, water | 20.00 |
| bisabolol | 0.30 |
| potassium hydroxide | 4.00 |
| BHT | 0.05 |
| EDTA-3Na | 0.05 |
| water | balance |
| total | 100.00 |

Blending Example 4 Facial Washing Powder

A facial washing powder blended as shown in the following Table 5 was prepared according to a conventional method.

TABLE 5

| | wt % |
|---|---|
| sodium lauroyl glutamate | 15.00 |
| sodium myristoyl glutamate | 15.00 |
| mannitol | 10.00 |
| talc | 20.00 |
| compound of Production Example 1 (10%) | 0.50 |
| cornstarch | 24.00 |
| glucose | 10.00 |
| sucrose | 5.00 |
| agar | 0.50 |
| total | 100.00 |

Blending Example 5 Natural Hair Shampoo

A natural hair shampoo blended as shown in the following Table 6 was prepared according to a conventional method.

TABLE 6

| | wt % |
|---|---|
| lauryl sulfoacetic acid | 4.00 |
| lauryl glucoside, water | 9.00 |
| sodium cocoyl glutamate, disodium cocoyl ethylhexylglycerol, phenoxyethanol, | 20.00 0.50 |
| glyceryl caprate | 3.00 |
| Lauroyl arginine | 0.40 |
| compound of Production Example 1 (10%) | 1.00 |
| flavor | q.s. |
| magnesium chloride | 1.50 |
| citric acid | 0.54 |
| water | balance |
| total | 100.00 |

Blending Example 6 Scalp Care Shampoo

A scalp care shampoo blended as shown in the following Table 7 was prepared according to a conventional method.

TABLE 7

|  | wt % |
|---|---|
| polyquaternium-10 | 0.40 |
| laurethammonium sulfate, water | 14.30 |
| cocamidopropyl betaine, water | 15.00 |
| disodium laureth sulfosuccinate, water | 5.00 |
| citric acid, cocamide MEA, glycol distearate, sodium dehydroacetate, propylparaben, methylparaben, sodium laureth sulfate, water | 5.00 |
| compound of Production Example 1 (10%) | 1.00 |
| PEG-7 glyceryl cocoate | 2.00 |
| PEG-150 distearate | 0.15 |
| flavor: dipropyleneglycol, citral, linalool, geraniol, butylphenylmethyl propanal | 0.20 |
| ginger root extract, butylene glycol, water | 0.10 |
| sodium benzoate | 0.20 |
| PCA zinc | 1.00 |
| sodium chloride | 1.20 |
| flavor | appropriate |
| water | balance |
| total | 100.00 |

Blending Example 7 Mild Hair Shampoo

A mild hair shampoo blended as shown in the following Table 8 was prepared according to a conventional method.

TABLE 8

|  | wt % |
|---|---|
| sodium laureth 4 carboxylate, water | 8.33 |
| macadamia nut fatty acid phytosteryl | 1.00 |
| dimer dilinoleic acid dimer dilinoleyl bis(phytosteryl/behenyl/isostearyl) | 0.10 |
| ethanol | 10.00 |
| compound of Production Example 1 (10%) | 1.00 |
| glycerol | 3.00 |
| argania spinosa kernel oil | 0.15 |
| sodium cocoyl methyl taurine, water | 15.00 |
| sodium cocoamphoacetate | 5.00 |
| polyquaternium-10 | 0.30 |
| citric acid | 0.10 |
| HEDTA-3Na | 0.05 |
| xanthan gum | 0.30 |
| water | balance |
| total | 100.00 |

Blending Example 8 Conditioning Hair Shampoo

A conditioning hair shampoo blended as shown in the following Table 9 was prepared according to a conventional method.

TABLE 9

|  | wt % |
|---|---|
| polyquaternium-10 | 0.20 |
| cocoyl alanine TEA, water | 20.00 |
| sodium lauroyl sarcosine, water | 4.20 |
| cocoyl arginine, water | 2.00 |
| sodium olefin (C14-16) sulfonate | 2.00 |
| cocobetaine, water | 6.00 |
| Lauramide DEA | 2.00 |
| cocamide methyl MEA | 0.50 |
| compound of Production Example 1 (10%) | 1.00 |
| polyquaternium-7 | 5.00 |

TABLE 9-continued

|  | wt % |
|---|---|
| citric acid | 0.10 |
| preservative | q.s. |
| water | balance |
| dioleic acid PEG-120 methylglucose | 1.50 |
| PEG-150 pentaerythrityl tetrastearate | 0.50 |
| (aminoethyl aminopropyl methicone/dimethicone) copolymer | 2.00 |
| PEG-3 distearate | 1.50 |
| flavor | q.s. |
| total | 100.00 |

Blending Example 9 Body Shampoo

A body shampoo blended as shown in the following Table 10 was prepared according to a conventional method.

TABLE 10

|  | wt % |
|---|---|
| lauric acid | 6.00 |
| myristic acid | 2.00 |
| palmitic acid | 2.00 |
| acrylates/C10-30 alkyl) crosspolymer | 0.70 |
| compound of Production Example 1 (10%) | 1.00 |
| sodium laureth sulfate, water | 6.20 |
| potash soap material, cocamide MEA, glycol distearate, water | 3.00 |
| polyquaternium-39 | 3.00 |
| cocamidopropyl betaine, water | 7.80 |
| glycerol | 5.00 |
| potassium hydroxide (85%) | 3.40 |
| sodium chloride | 2.50 |
| DMDM hydantoin | 0.20 |
| EDTA-2Na | 0.10 |
| flavor | appropriate |
| water | balance |
| total | 100.00 |

The cosmetics of Blending Examples 1-9 were all superior in quick foaming, foam volume, quick rinsing performance and smooth feeling after drying.

The details of the materials used are as follows. sodium cocoyl glycinate, water: AMILITE GCS-12K (30%) (manufactured by Ajinomoto Co., Inc.)

xanthan gum: KELTROL CG-T (manufactured by CP Kelco)

glycerol: concentrated glycerin for cosmetic (manufactured by Kao Corporation)

cocoglucoside, water: PLANTACARE 818up (50%) (manufactured by BASF)

lauramidopropyl betaine, water: softazoline LPB (30%) (manufactured by KAWAKEN fine chemicals Co., Ltd.)

sodium cocoyl glutamate, disodium cocoyl glutamate, water: Amisoft CS-22 (30%) (manufactured by Ajinomoto Co., Inc.)

cocobetaine, water: dehyton AB30 (30%) (manufactured by BASF)

sodium cocoamphoacetate, water: Miranol Ultra C32 (32%) (manufactured by Rhodia)

glyceryl caprylate: Sunsoft No.700P-2 (manufactured by Taiyo Kagaku)

propanediol: Zemea propanediol (manufactured by DOW)

jojoba oil: purification jojoba oil (manufactured by KOEI KOGYO Co., Ltd.)

almond oil: NIKKOL sweet almond oil (manufactured by Nikko Chemicals)

guar gum: JAGUAR S (manufactured by Rhodia)

sodium lauryl glycol carboxylate, water: BEAULIGHT SHAA (30%) (manufactured by Sanyo Chemical Industries, Ltd.)
phytosteryl/octyldodecyl lauroyl glutamate: ELDEW PS-203R (manufactured by Ajinomoto Co., Inc.)
sorbitol: (manufactured by Kao Corporation)
PEG-32 (polyethylene glycol-32): PEG #1500 (manufactured by NOF)
beeswax: WHITEBEES WAX (manufactured by Miki Chemical Industry & Co., Ltd.)
stearic acid: NAA-180 (manufactured by NOF)
lauric acid: NAA-122 (manufactured by NOF)
myristic acid: NAA-142 (manufactured by NOF)
poloxamer 184: PLONON #184 (manufactured by NOF)
isostearic acid PEG-90 glyceryl: EMALEX GWIS-190 (manufactured by Nihon Emulsion Co., Ltd.)
glyceryl stearate (SE): EMALEX GMS-2E (manufactured by Nihon Emulsion Co., Ltd.)
sodium methyl cocoyl taurate, water: NIKKOL CMT-30 (30%) (manufactured by Nikko Chemicals)
lauryl betaine, water: NIKKOL AM-301 (30%) (manufactured by Nikko Chemicals)
bisabolol: bisabolol nat (manufactured by BASF)
BHT (dibutylhydroxytoluene) EDTA-3Na (ethylenediaminetetraacetic acid trisodium salt trihydrate): Dissolvine NA3-36 (36%) (manufactured by AKZO NOBEL)
sodium lauroyl glutamate: Amisoft LS-11 (manufactured by Ajinomoto Co., Inc.)
sodium myristoyl glutamate: Amisoft MS-11 (manufactured by Ajinomoto Co., Inc.)
mannitol: Marin Crystal (manufactured by Towa chemical industry)
talc: MICRO ACE P-3 (manufactured by Japan talc)
cornstarch: ST starch C(W) (manufactured by NIPPON STARCH CHEMICAL CO., LTD.)
agar: agar preparation RS-400 (manufactured by MARINE SCIENCE CO., LTD)
lauryl sulfoacetic acid: NIKKOL LSA-F (manufactured by Nikko Chemicals)
lauryl glucoside, water: PLANTACARE 1200up (50%) (manufactured by BASF)
sodium cocoyl glutamate, disodium cocoyl glutamate, water: Amisoft CS-22 (25%) (manufactured by Ajinomoto Co., Inc.)
ethylhexyl glycerol, phenoxyethanol, tocopherol: Euxyl PE9010 (manufactured by Schulke & Mayr)
glyceryl caprate: Sunsoft No. 760 (manufactured by Taiyo Kagaku)
lauroyl arginine: AMISAFE AL-01 (manufactured by Ajinomoto Co., Inc.)
polyquaternium-10: UCARE Polymer JR400 (manufactured by DOW)
laurethammonium sulfate, water: Sulfochem EA-2 (2 mole) Surfactant (25%) (manufactured by Lubrizol Advanced Materials)
cocamidopropyl betaine, water: AMPHITOL 55AB (30%) (manufactured by Kao Corporation)
disodium laureth sulfosuccinate, water: Texapon SB-3 (30%) (manufactured by BASF)
citric acid, cocamide MEA, glycol distearate, sodium dehydroacetate, propylparaben, methylparaben, sodium laureth sulfate, water: DN-P conc (manufactured by Dainihonkasei)
PEG-7 glyceryl cocoate (coconut oil fatty acid PEG-7 glyceryl): Cetiol HE (manufactured by BASF)
PEG-150 distearate: EMANON 3299V (manufactured by Kao Corporation)
ginger root extract, butylene glycol, water: zingiber officinale root extract-BG (yamadayaken co. ltd) PCA zinc (zinc salt of pyrrolidonecarboxylic acid): AJIDEW ZN-100 (manufactured by Ajinomoto Co., Inc.)
sodium laureth-4 carboxylate, water: BEAULIGHT LCA-30D (30%) (manufactured by Sanyo Chemical Industries, Ltd.)
macadamia nut fatty acid phytosteryl: YOFCO MAS (Nippon Fine Chemical)
dimer dilinoleic acid dimer dilinoleyl bis(phytosteryl/behenyl/isostearyl): Plandool G (manufactured by Nippon Fine Chemical)
ARGANIA SPINOSA KERNEL oil: Argan Organic Oil (manufactured by Greentech S. A.)
HEDTA-3Na (trisodium hydroxyethylethylenediamine triacetate): Chelest H-SD(manufactured by Chubu Chelest)
cocoyl alanine TEA, water: AMILITE ACT-12L (30%) (manufactured by Ajinomoto Co., Inc.)
sodium lauroyl sarcosine, water: Soypon SLE (39%) (manufactured by KAWAKEN fine chemicals co., Ltd.)
cocoyl arginine (coconut oil fatty acid arginine), water: Aminosoap AR-12 (manufactured by Ajinomoto Co., Inc.)
sodium olefin(C14-16) sulfonate: Liporan PJ-400 (manufactured by Ajinomoto Co., Inc.)
cocobetaine, water: Obazolin BC (30%)(manufactured by Toho chemical industry)
lauramide DEA (lauric diethanolamide): Amisole LDE (manufactured by KAWAKEN fine chemicals co., Ltd.)
cocamide methyl MEA (coconut oil fatty acid N-methyl-monoethanolamide): Aminon 011-S (manufactured by Kao Corporation)
polyquaternium-7: Lipoflow MN (5%) (manufactured by Lion Corporation)
PEG-120 methyl glucose dioleate: Glucamate DOE-12 Thickener (manufactured by Lubrizol Advanced Materials)
PEG-150 pentaerythrityl tetrastearate: CROTHIX (manufactured by Croda)
(aminoethylaminopropylmethicone/dimethicone) copolymer: XF42-B1989 (manufactured by Momentive Performance Materials)
PEG-3 distearate: Estepearl 30 (manufactured by Nikko Chemicals)
palmitic acid: NAA-160 (manufactured by NOF)
acrylates/C10-30alkyl)crosspolymer: Carbopol SC-200 Polymer (manufactured by Lubrizol Advanced Materials) sodium laureth sulfate, water: Texapon N-70 (70%) (manufactured by BASF)
potash soap material, cocamide MEA, glycol distearate, water: amphorex ASH (manufactured by Miyoshi-Yushi)
polyquaternium-39: Merquat Plus 3330 (manufactured by Lubrizol Advanced Materials)
DMDM hydantoin: Glydant (manufactured by Lonza)
EDTA-2Na (ethylenediaminetetraacetic acid disodium salt dihydrate): Dissolvine NA2 (manufactured by AKZO NOBEL)

INDUSTRIAL APPLICABILITY

The present invention can provide a composition superior in foamability and foam volume and affording improved rinsing performance and smooth feeling after drying.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A composition, comprising:
   (A) at least one compound represented by formula (1)

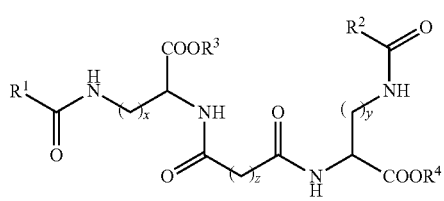

wherein
   $R^1$ and $R^2$ are each independently an alkyl group having 5 to 21 carbon atoms or an alkenyl group having 5-21 carbon atoms,
   $R^3$ and $R^4$ are each independently a hydrogen atom, an alkyl group having 1 to 22 carbon atoms or an alkenyl group having 2 to 22 carbon atoms,
   z 8,
   x and y are each independently an integer of 2 to 4, or a salt thereof; and
   (B) at least one kind of surfactant selected from the group consisting of an anionic surfactant having a carboxyl group, an amphoteric surfactant, and a nonionic surfactant.

2. The composition according to claim 1, wherein in said formula (1) x and y are each 4.

3. The composition according to claim 1, wherein in said formula (1) $R^1$ and $R^2$ are each independently a straight-chain alkyl group having 5 to 15 carbon atoms.

4. The composition according to claim 1, wherein in said formula (1) wherein $R^3$ and $R^4$ are each a hydrogen atom.

5. The composition according to claim 1, wherein in said formula (1) $R^1$ and $R^2$ are each independently a straight-chain alkyl group having 5 to 15 carbon atoms, $R^3$ and $R^4$ are each a hydrogen atom, and x and y are each 4.

6. The composition according to claim 1, wherein (A) said at least one compound represented by formula (1) is a disodium salt.

7. The composition according to claim 1, wherein said (A) is at least one compound selected from the group consisting of bis($N^\varepsilon$-lauroyl-L-lysine)sebacoyl amide, a salt of bis($N^\varepsilon$-lauroyl-L-lysine)sebacoyl amide, bis($N^\varepsilon$-octanoyl-L-lysine)sebacoyl amide, and a salt of bis($N^\varepsilon$-octanoyl-L-lysine)sebacoyl amide.

8. The composition according to claim 1, wherein said (A) is present in a proportion of 0.01 to 10 wt % relative to the total weight of the composition.

9. The composition according to claim 1, wherein said anionic surfactant having a carboxyl group is at least one kind selected from the group consisting of a fatty acid salt, an alkyl ether carboxylate, a hydroxyalkyl ether carboxylate, an acyl acidic amino acid salt, and an acyl neutral amino acid salt.

10. The composition according to claim 1, wherein said amphoteric surfactant is at least one kind selected from the group consisting of an amino acetic acid betaine surfactant, an imidazolinium betaine surfactant, an alkyl betaine surfactant, a fatty acid amidopropyl betaine surfactant, and a sultaine surfactant.

11. The composition according to claim 1, wherein said nonionic surfactant is at least one alkyl polyglucoside.

12. The composition according to claim 1, wherein said (B) is present in a proportion of 0.01 to 50 wt % relative to the total weight of the composition.

13. A cleaning agent, comprising a composition according to claim 1.

14. The composition according to claim 1, wherein said (A) at least one compound represented by formula (1) is bis($N^\varepsilon$-lauroyl-L-lysine)sebacoyl amide disodium salt.

15. The composition according to claim 1, wherein said (A) at least one compound represented by formula (1) is bis($N^\varepsilon$-octanoyl-L-lysine)sebacoyl amide disodium salt.

* * * * *